United States Patent
Chiang et al.

(10) Patent No.: US 6,508,776 B2
(45) Date of Patent: Jan. 21, 2003

(54) COMPRESSION BRACE STRUCTURE AND MATERIAL

(75) Inventors: Jackson Chiang, Taipei (TW); Jonathon Chuang, Brisbane (AU)

(73) Assignee: La Pointique International Ltd., Tukwila, WA (US)

( * ) Notice: Subject to any disclaimer, the term of this patent is extended or adjusted under 35 U.S.C. 154(b) by 0 days.

(21) Appl. No.: 09/846,332

(22) Filed: May 2, 2001

(65) Prior Publication Data

US 2002/0165474 A1 Nov. 7, 2002

(51) Int. Cl.$^7$ ................................................. A61F 5/00
(52) U.S. Cl. ........................... 602/5; 602/60; 602/61
(58) Field of Search ........................... 602/2, 5, 13, 14, 602/20, 21, 60, 42, 59, 61–63; 428/67, 116

(56) References Cited

U.S. PATENT DOCUMENTS

| | | |
|---|---|---|
| 2,570,182 A | 10/1951 | Daly et al. |
| 2,653,601 A | 9/1953 | Morrison |
| 2,976,539 A | 3/1961 | Brown, Jr. |
| 3,092,110 A | 6/1963 | Duensing |
| 3,451,232 A | 6/1969 | Belzidsky |
| 3,600,717 A | 8/1971 | McKeehan |
| 3,892,239 A | 7/1975 | Masso Remiro |
| 3,990,440 A | 11/1976 | Gaylord, Jr. |
| 3,991,424 A | 11/1976 | Prahl |
| 4,043,058 A | 8/1977 | Hollister et al. |
| 4,084,586 A | 4/1978 | Hettick |
| 4,153,054 A | 5/1979 | Boone |
| 4,272,850 A | 6/1981 | Rule |
| 4,294,240 A | 10/1981 | Thill |
| 4,470,411 A | 9/1984 | Hoyt, Jr. |
| 4,516,572 A | 5/1985 | Schlein |
| 4,690,847 A | 9/1987 | Lassiter et al. |
| 4,832,010 A | 5/1989 | Lerman |
| 5,020,164 A | 6/1991 | Edwards |
| 5,449,341 A * | 9/1995 | Harris .......................... 602/63 |
| 5,489,259 A * | 2/1996 | Jacobs .......................... 602/13 |
| 5,656,352 A | 8/1997 | Middleton |
| 5,658,324 A * | 8/1997 | Bailey .......................... 607/104 |
| 5,735,807 A | 4/1998 | Cropper |
| 5,901,379 A | 5/1999 | Hirata |
| 5,924,134 A | 7/1999 | Taylor et al. |
| 6,093,468 A | 7/2000 | Toms et al. |
| 6,110,135 A | 8/2000 | Madow et al. |
| 6,129,695 A | 10/2000 | Peters et al. |

FOREIGN PATENT DOCUMENTS

| | | |
|---|---|---|
| GB | 1094893 | 12/1967 |
| GB | 2 312 643 A | 11/1997 |

* cited by examiner

*Primary Examiner*—Michael A. Brown
(74) *Attorney, Agent, or Firm*—Christensen O'Connor Johnson Kindness PLLC

(57) ABSTRACT

The present invention provides a composite material for use in making orthopedic elastic braces for supporting a body part by compression. The composite material includes center (110), inner (120), and outer layers (130). The center layer having on one side a plurality of grooves (100) that intersect each other to define a grid pattern functioning as passageways along the width and length of the layer to promote heat and moisture dissipation for the body part being supported. A plurality of cuts (150) extending through the entire depth of the center layer and distributed across the surface area of the layer, while retaining sufficient elasticity and density to provide adequate compression support.

18 Claims, 5 Drawing Sheets

COMPRESSION BRACE STRUCTURE AND MATERIAL

FIELD OF THE INVENTION

This invention generally relates to orthopedic supports and, more specifically, to a composite material for use in making elastic compression braces having improved compression support, body heat retention and breathability during use.

BACKGROUND OF THE INVENTION

Elastic compression braces are available in many forms. Commonly such braces are composed of soft, elastic material so that when worn, they provide a certain amount of support for an injured joint. These types of brace, often purchased without a prescription or the need for skilled professional fitting, have been used for a number of years and have been commonly available as braces for the knee, ankle, thigh, wrist, elbow, chest or lower back. These resilient, pliable compression braces can be worn for sprains and strains, arthritis, tendonitis, bursitis, inflammation, or to reduce discomfort during post-operative use or to treat post-trauma discomfort.

The elastic compression braces are often made from synthetic rubber (e.g., polychloroprene). This particular material is desirable because of its combination of favorable properties useful in elastic compression braces. Polychloroprene rubber has good elasticity and a relatively high density, thereby providing good compression support and resistance to shear forces.

Polychloroprene rubber is a closed cell material and therefore does not dissipate heat very well during use. Its closed cell characteristics can be useful in retaining heat during use by reflecting emitted heat back into the bones and joints of he affected area. This localized concentration of heat can aid venous flow, help educe edema, and make the soft tissues less susceptible to injury.

Although use of polychloroprene rubber in elastic compression braces can concentrate heat, the natural tendency of the closed cell material to prevent heat dissipation may cause problems for the user. When worn, the polychloroprene material braces are stretched to impart a compression load around the affected body area. This compression fit, combined with the high density of the material and the lack of air circulation and dissipation through the material, can result in heat discomfort and perspiration and may lead to heat rashes. Prolonged use of such braces can cause the user to perspire constantly, resulting in discomfort to such a degree that the user often stops wearing the brace prematurely. In effect, the material itself dictates the length of time that the orthopedic brace can be worn. It is not uncommon for users to stop wearing such braces after about one to two hours. In an effort to provide better breathability, certain prior polychloroprene rubber braces have been manufactured with perforations or holes punched through the entire depth of the material. However, these braces may not retain sufficient structural integrity to serve as an effective compression brace for the wearer because neoprene material is removed from these braces.

Thus, there is a need for an elastic compression brace having sufficient structural strength and integrity to offer a sufficient level of compression support, while also dissipating heat during use to reduce or avoid undue perspiration and heat discomfort, especially during prolonged use.

SUMMARY OF THE INVENTION

The present invention provides a flexible, resilient composite material for use in forming elastic compression braces for surrounding and supporting a body part by compression. The composite material includes a center elastic layer, an inner fabric layer and an outer fabric layer. The elastic center layer is preferably composed of closed cell material in sheet form, having on one side thereof a plurality of grooves or channels formed therein to intersect each other to define a gridwork. The pattern of channels provides passageways along the width and length of the center layer to enable heat and moisture dissipation for the body part being supported.

The center layer also may have a plurality of cuts extending through the entire depth of the layer and distributed across the surface area of the layer, with the center layer still having sufficient structural strength and integrity to provide orthopedic compression support.

The composite material may also include an inner layer of flexible, resiliently elastic, porous fabric material bonded to the grooved side of the center layer. The outer fabric layer may also be composed of a flexible, resiliently elastic, porous material bonded to the non-grooved side of the center layer.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
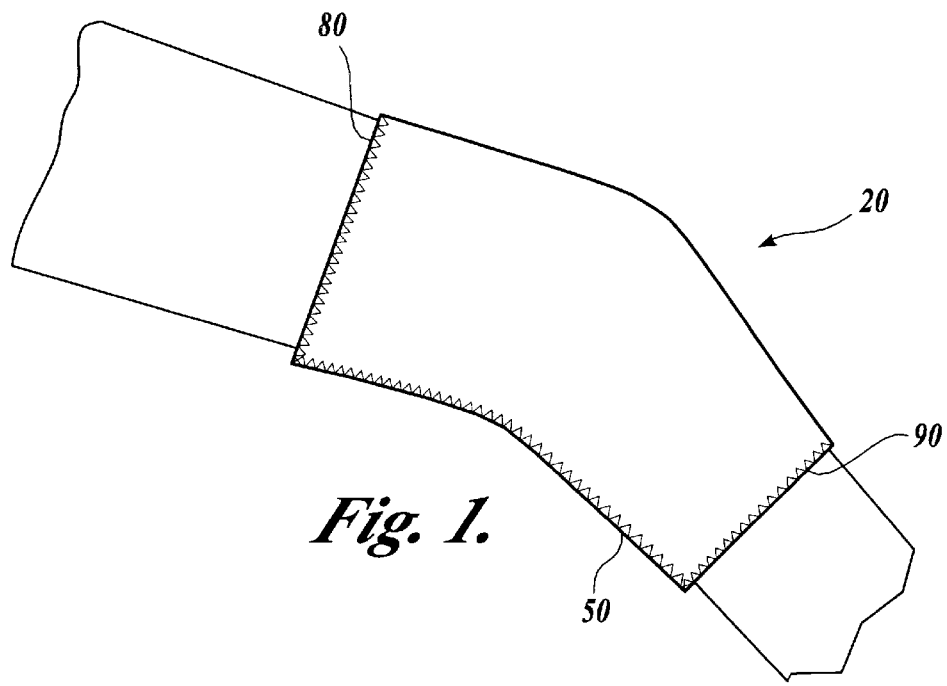
FIG. 1 is a side elevation view semi-schematically illustrating a knee brace made from an orthopedic material according to principles of the present invention.
Figure 2:
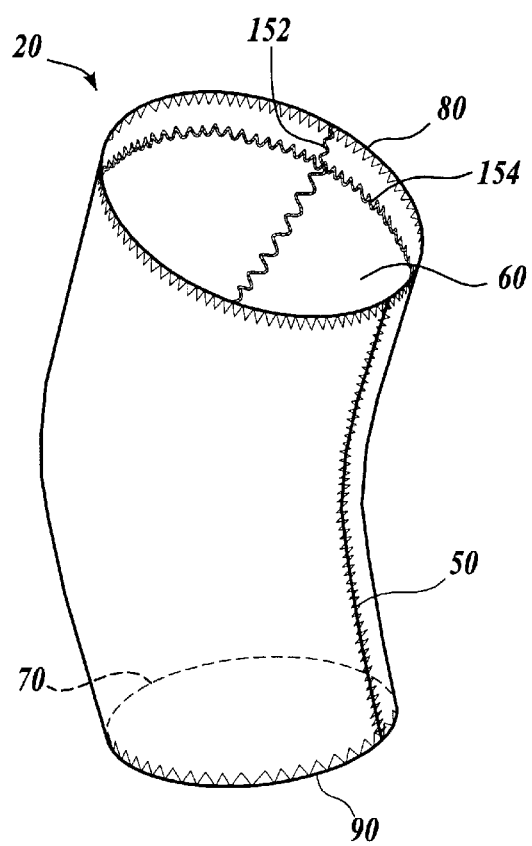
FIG. 2 is a semi-schematic perspective view of the knee brace shown in FIG. 1.
Figure 3:
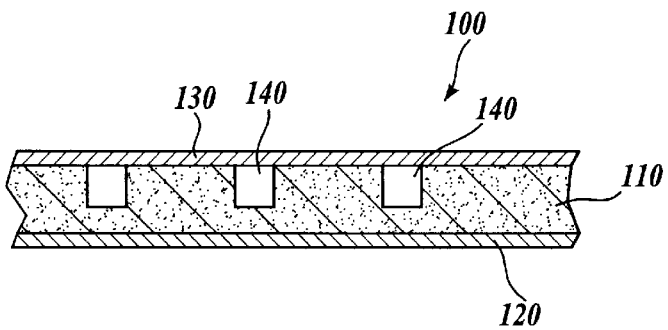
FIG. 3 is a cross-sectional view schematically illustrating components of a composite orthopedic material of the present invention.
Figure 4:
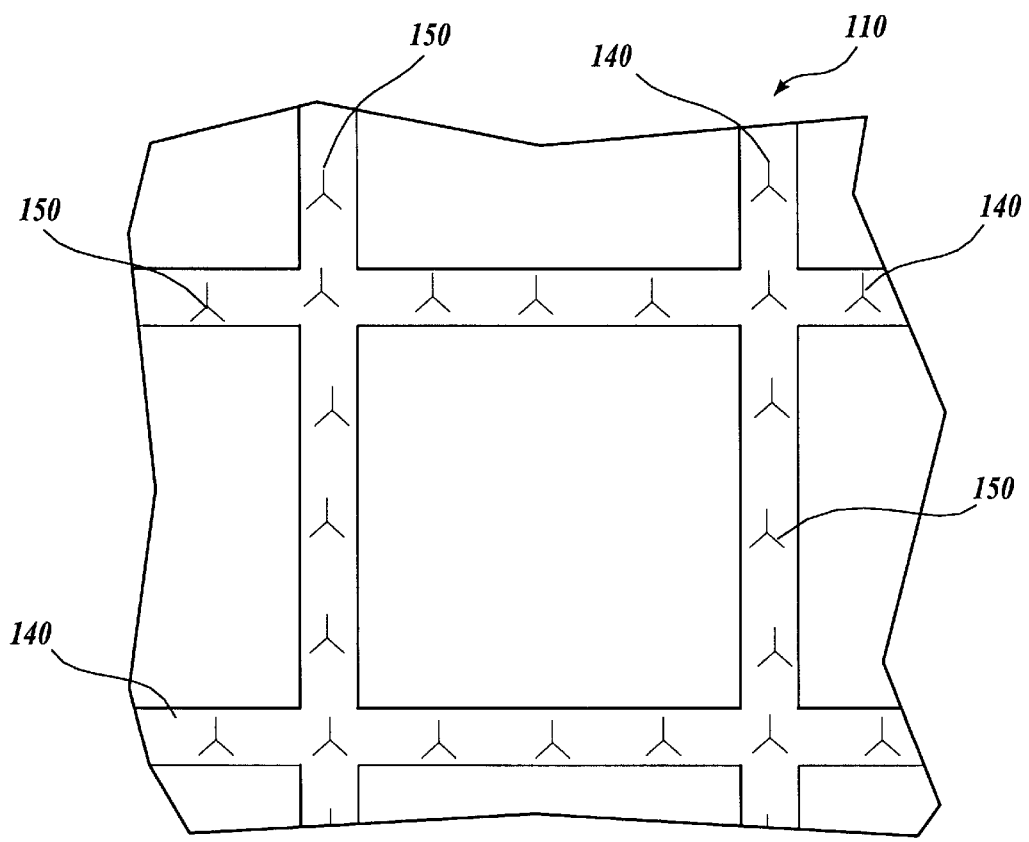
FIG. 4 is a frontal plan view illustrating a section of a punctured center layer of the composite material of the present invention.
Figure 5:
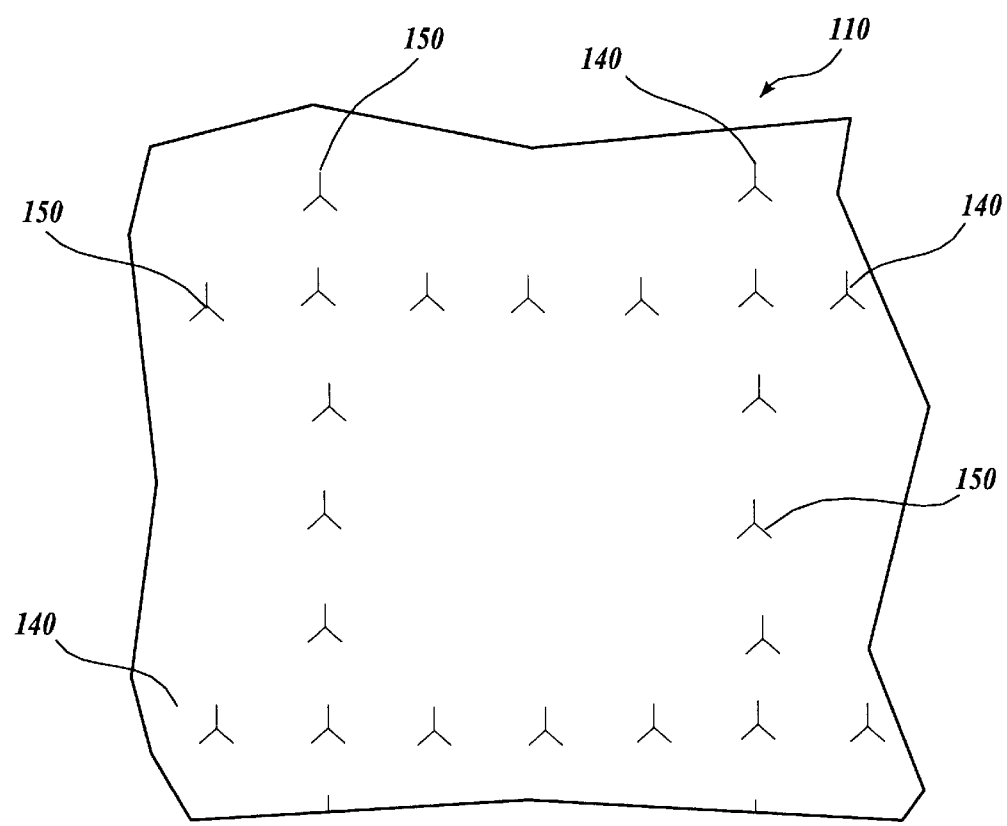
FIG. 5 is a back plan view illustrating a section of the punctured center layer shown in FIG. 4.

FIGS. 1 and 2 illustrate a knee brace 20 made from an orthopedic material according to principles of this invention. The orthopedic material is illustrated in FIGS. 3, 4 and 5. The knee brace is a soft orthopedic brace made from a flexible, resilient composite 100 shown in flat form in FIGS. 3, 4 and S. The flat form composite material is cut to shape and sewn or otherwise assembled to so form a tubular knee brace 20, illustrated in FIGS. 1 and 2.

Referring to FIGS. 1 and 2, a piece of composite material 100 in flat sheet form is folded over on itself. The overlapping long edges on the opposite side of the fold are fastened by a long, upright seam 50. The material in the flat is cut in a shape so that when stitched along seam 50, as shown in FIGS. 1 and 2, an angular knee support of generally tubular form is produced having an open top 60 and an open bottom 70. Peripheral stitching 80 at the upper edge and similar peripheral stitching 90 at the bottom edge provide finished edges for the completed knee support.

The components which comprise the composite 100 are best understood by referring to FIGS. 3, 4 and 5. FIG. 3 shows a cross-sectional view illustrating the components of the composite 100 of the present invention. The composite material includes a flexible and foldable center elastic layer 110, an inner fabric layer 130, and an outer fabric layer 120. The center elastic layer 110 is preferably from a closed cell foam material in sheet configuration. One preferred elastic closed cell material is polychloroprene rubber, commonly known as neoprene rubber. Preferred neoprene materials are articles of commerce. Another suitable material for center layer 110 is Styrene Butadiene Rubber (SBR). These materials are available in a wide density range so it is not difficult to find material of a desired density that provides the desired level of support and provides good orthopedic compression during use. Ideally such material for the purposes of the present invention is from 15 mm to 8 mm thick. However, other thicknesses may be used. Also, other elastic closed cell materials may be used to form layer 110.

The center elastic layer 110 has formed therein on one side thereof a plurality of intersecting grooves or channels 140. In non-limiting example, one embodiment of the present invention shows the pattern of intersecting channels 140 is formed by placing neoprene sheet material down on a metal mesh and then placing a weighted heat source on top of the flat sheet material. The pressure and heat cause the mesh to depress into the sheet material to permanently take the shape of the metal mesh on the underside where the grid pattern of the metal mesh is pressing into the sheet material. In addition or alternatively, the mesh may be preheated.

In another embodiment of the present invention, a pattern of intersecting channels 140 is formed on both surfaces of the sheet material. This can be accomplished in one manner by sandwiching the center layer 110 between top and bottom metal grids and heat pressing both grids against center layer 110, causing both grids to depress into the surfaces of the sheet material. The grid pattern may be identical on both sides of the center layer 110, or may be of different configurations.

In the embodiment shown in FIGS. 3 and 4, the plurality of intersecting channels 140 formed in center elastic layer 110 define a generally rectangular or square-shaped pattern or grid. It is to be appreciated that the pattern can be of any other shape (e.g. diamonds (see FIG. 9), triangles, ovals, circles, etc.) as long as the channels 140 intersect each other so as to provide a continuous or interconnected passageway across the sheet material and along the length of the material.

The center elastic layer 110 may be punctured to form a multiplicity of punctures or cuts 150 through the layer. Cuts 150 are not shown in FIG. 3 for simplicity but are shown in FIGS. 4 and 5. FIG. 4 is a frontal plan view showing a section of punctured center layer 110. FIG. 5 is a back plan view showing a section of the punctured center layer 110 shown in FIG. 4. The multiplicity of cuts 150 are dispersed across the surface of center elastic layer 110 and extend through the entire depth of the layer so that fluids, including perspiration and air, can pass through the cuts 150 from one side of the layer to the other, especially when the layer is stretched.

In one embodiment of the present invention, cuts 150 are located only in registry with the channel portions 140. In another embodiment, cuts 150 are located not only within the channels 140, but also in the ungrooved/channeled portion of elastic layer 110. In a further embodiment, the cuts 150' are located only at the intersections of the channels 140'. The multiplicity of cuts 150 may be of uniform pattern and spaced apart uniformly about the center elastic layer 110. Ideally, the multiplicity of cuts 150 should not be so large or the cuts must be spaced so close together that the overall structural integrity of the neoprene material is reduced beyond the ability of the material to provide sufficient orthopedic compression support during use.

The multiplicity of cuts 150 may define a cut pattern. FIGS. 4 and 5 show that the cut pattern has three "legs" that radiate from a common point. It is to be appreciated, however, that the cut pattern may be any shape such as a straight line, a curved line, a cross, or a five-legged pattern, without departing from the scope of the present invention. It is to be further appreciated that preferably the puncture does not actually remove any significant material, if any, from center elastic layer 110 or channels 140; rather, the puncture simply extends through the channels. Thus, the puncture does not form a hole or passage through the neoprene material unless the material is stretched.

The pattern for the multiplicity of cuts 150 may be formed in center elastic layer 110 by a number of methods. One such method of forming a cut pattern in the neoprene material is by a roller having a cylindrical outer surface with projecting punches in the desired cut pattern so that rolling the roller over the flat surface of the neoprene material punches out cuts in the desired pattern.

Referring back to FIG. 3, composite material 100 also includes a soft, flexible, resilient, porous inner fabric layer 130. Inner layer 130 may be a knitted flexible and foldable, stretchable cloth fabric material which is porous to air and water because of the pores inherently formed by the knitted fabric. Composite material 100 also includes a flexible and elastic, porous outer fabric layer 120 which also may be made from a stretchable knitted fabric of the same or different type from layer 130. The inner and outer fabric layers 130 and 120, respectively, may also be made from other stretchable knitted fabrics including nylon, Dacron or other synthetic fibers.

After the center elastic layer 110 is altered with a plurality of intersecting channels 140 on one side thereof and punctured with a cut pattern 150, inner fabric layer 130 is bonded to the grooved face of center layer 110 while outer fabric layer 120 is bonded to the non-grooved face of center layer 110. Inner fabric layer 130 may be adhered to the center layer 110 using an adhesive technique that prevents the glue or other adhesive from being placed in channels 140. As such, the adhesive does not close or obstruct channels 140. Outer fabric layer 120 is also glued or otherwise adhered or bonded to center layer 110. The adhesive bonds the entire contacting surface areas of the center layer 110 and the adjoining inner and outer fabric layers 130 and 120, respectively. It is to be noted that the adhesive does not disrupt the porosity of the center layer 110 and the inner or outer layers 130 and 120.

Returning to FIGS. 1 and 2, knee brace 20 is intended to be worn with the grooved/channeled side facing the body of the wearer. This provides the advantageous result of retaining heat against the body while allowing knee brace 20 to be breathable. Furthermore, because knee brace 20 is made from the composite material, it has sufficient porosity that internal heat build-up during use is essentially avoided. Knee brace 20 also provides good compression around a body part supported by knee brace 20 in its stretched condition. The elastic center layer retains substantially all of its ability to apply a compression load on the body portion being braced because material is not actually removed from the neoprene center layer as in some conventional braces. Additionally, knee brace 20 is of sufficient density due to the neoprene, SBR or other selected material to provide the compression necessary to serve as a useful knee brace. The inner and outer layers 130 and 120 also provide additional compressive strength to knee brace 20.

Knee brace 20 also provides good breathability. When knee brace 20 is in use, it stretches in a bi-directional manner, thereby creating a pumping action to allow air to flow through the channels 140 of knee brace 20. This carries body sweat through channels 140 and out the ends of knee brace 20. Knee brace 20 also allows fresh, cool air to pass inwardly through knee brace 20 to reach the body. Correspondingly, a certain amount of heat is able to pass from inside knee brace 20 to the outside through the plurality of cuts 150, which open up as the brace is stretched during use.

In accordance with a further aspect of the present invention, silicone 152, in the form of a gel or beads, may be applied along the inside of knee brace 20 lengthwise of the brace, perhaps on opposite sides of the brace. Additionally or alternatively, the silicone beads 154 may be placed circumferentially around the inside of the brace, perhaps near the ends of the brace. The silicone may be applied in a stripe of some width, in a narrow line or band or in other patterns. Moreover, the stripe or line of silicone may be straight or curved. This silicone material causes the brace to stay in place on the body due to the friction between the silicone and the body. The silicone does not, however, cause discomfort or undue rubbing against the body.

In one embodiment, the silicone may be applied to the interior of knee brace 20 after the brace has been fully constructed. In another embodiment, the silicone is applied to the inside of inner fabric layer 130 of knee brace 20 and then the inner layer 130 is applied to the inside surface of center layer 110. As those skilled in the art will appreciate, other materials, in addition to silicone, may be employed to cause the brace to stay in place on the body without departing from the scope of the present invention.

Figure 6:
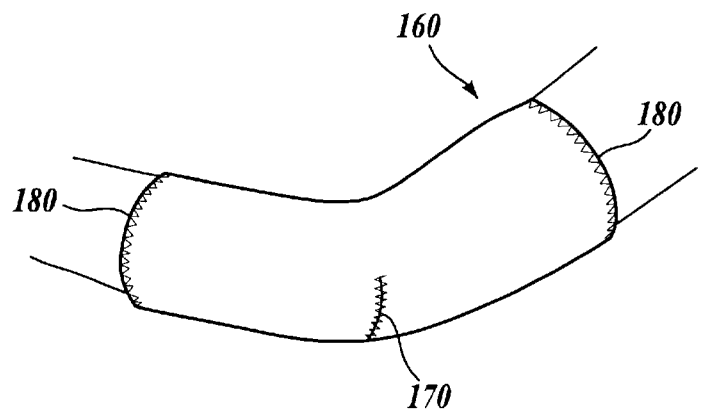
FIG. 6 is a perspective view illustrating an elbow brace made from the composite material of the present invention.
Figure 7:
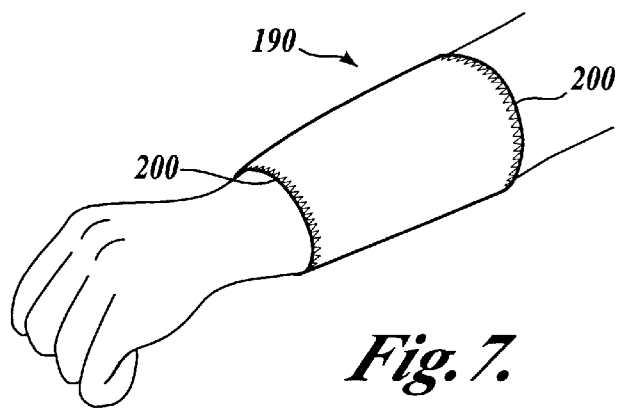
FIG. 7 is a perspective view illustrating a wrist brace made from the composite material of the present invention.
Figure 8:
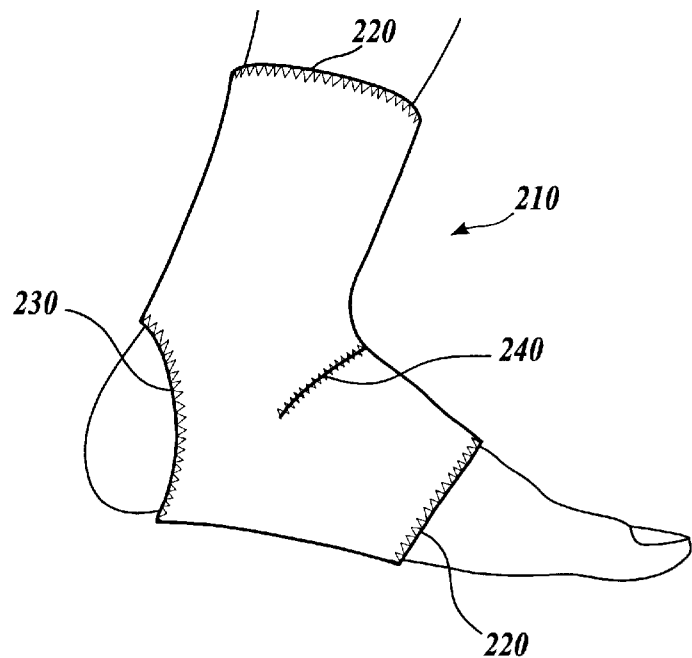
FIG. 8 is a side view illustrating an ankle brace made from the composite material of the present invention.

FIGS. 6 through 8 illustrate further uses of the composite material 100 in compression braces. FIG. 6 shows an elbow brace 160 in which composite material 100 is folded and seamed along its length. The brace may have an intermediate seam 170 to form a generally L-shaped tubular elastomeric brace. The top and bottom edges of the tubular brace have stitched peripheral seams 180 for edge reinforcement. FIG. 7 illustrates a wrist brace 190 made from the composite material 100 in which the material is folded and seamed lengthwise to form a generally straight tubular brace having peripheral stitching 200 at its opposite ends for edge reinforcement. FIG. 8 illustrates an ankle brace 210 made from composite material 100. The ankle brace 210 is formed as a generally L-shaped tubular brace with peripheral stitching 220 at its opposite ends, peripheral stitching 230 around an edge portion of the brace that fits around the heel of the user. The brace may include intermediate stitching 240 fastening adjoining intermediate edges of the L-shaped ankle support.

These compression braces can be used to provide required levels of anatomical compression support while improving ventilation to the supported area to reduce the discomfort caused by perspiration and over-heating. The improved composite material of this invention thus improves the anatomical support provided by compression braces formed when such materials build up, because the user is able to wear the brace for extended periods rather than having removed the brace prematurely because of heat discomfort.

Figure 9:
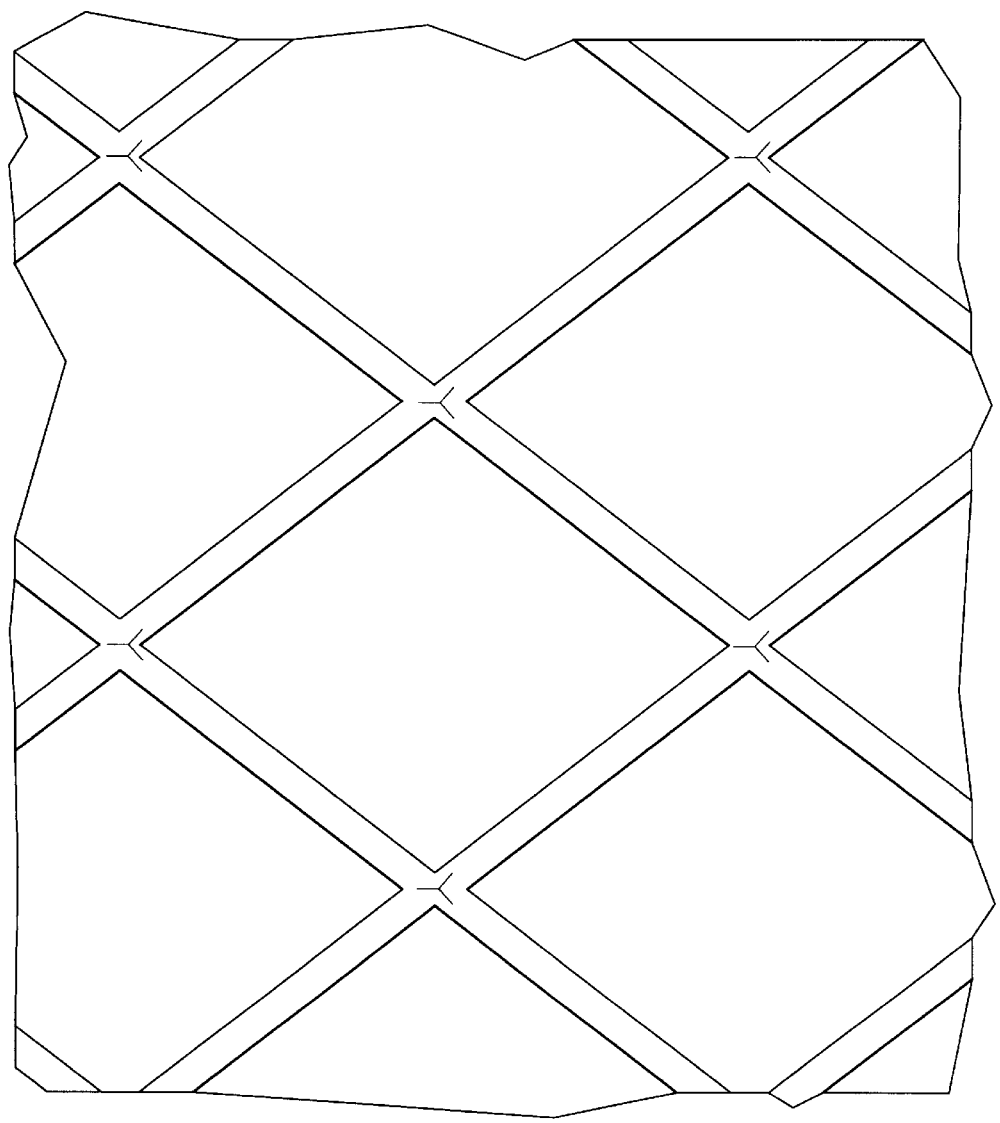
FIG. 9 is a view similar to FIG. 4, illustrating another pattern of channels formed in the center layer of the composite material.

FIG. 9 illustrates an alternative embodiment to the present invention wherein the composite material 100' is formed with an elastic center layer 110 having intersecting channels formed therein in a diamond pattern. Also, the cuts 150' are located at the intersection of the channels 140. The channels 140' and cuts 150' may be formed in a same or similar manner as described above with respect to center layer 110. Further, in other respects, the composite material 100' may be the same or similar to material 100 described above.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A flexible, resilient composite material used to manufacture elastic compression braces, the composite material comprising:

a center layer of elastic material having a first face and a second opposite face, a plurality of channels formed in the first face of the center layer, said channels intersecting each other to define a network, said plurality of channels defining passageways extending along substantially the entire length of said first face, and further wherein said center layer having a plurality of cuts extending through said center layer material;

an inner fabric layer of a resiliently elastic porous fabric attached to the first channeled face of said center layer; and an outer fabric layer of a resiliently elastic porous fabric attached to the second face of said center layer;

wherein said channels formed in the first face of the center layer are capable of channeling away moisture and heat when the first face side of said center layer is worn facing the wearer, and wherein when the center layer is stretched during use, the cuts in the center layer expand to allow passage of moisture and air therethrough.

2. The composite material of claim 1, wherein the plurality of channels define passages along substantially the entire width of said first layer.

3. The composite material of claim 1, wherein the channels are of substantially uniform depth.

4. The composite material of claim 3, wherein the channels are of a depth from about 1 mm to about 7 mm.

5. The composite material according to claim 4, wherein the channels are of a width of approximately 1 mm to approximately 4 mm.

6. The composite material of claim 1, wherein said plurality of channels may define any one of number of shaped patterns.

7. The composite material of claim 1, wherein said plurality of intersecting channels are formed on both the first and second faces of the center layer.

8. The composite material of claim 1, wherein said plurality of cuts are located only along said plurality of channels.

9. The composite material of claim 1, wherein said plurality of cuts define one or more of any number of cut patterns.

10. The composite material of claim 1, wherein said plurality of cuts are positioned about the surface of said center layer, including between the channels, so as not to reduce the overall density of said center layer beyond the ability of said center layer to provide sufficient orthopedic compression support during use.

11. The composite material of claim 1, wherein said inner and outer layers comprise knitted fabrics having pores naturally formed in the fabric.

12. The composite material of claim 1, wherein said center layer comprises polychloroprene rubber.

13. A compression brace for supporting the knee, elbow, wrist, or the like, made from said composite material of claim 1, wherein said composite material is shaped and seamed to form a tubular support open at both ends.

14. The brace of claim 13, further comprising silicone material applied therein to bear against the wearer to help cause said brace to stay in place on the wearer by the friction produced between said silicone and the wearer.

15. The brace of claim 14, wherein the silicone material is applied in the form selecting from the group consisting of one or more beads extending along the fabric layer, and liquid gel extending along the fabric layer.

16. The composite materials of claim 1, wherein said inner layer is bonded to the channeled first face of said center layer with a bonding agent, and said outer layer is bonded to the second face of said center layer, with the bonding agent, the bonding agent not located in said plurality of channels.

17. A flexible, resilient sheet material for use in making elastic compression braces for surrounding and supporting a body part by compression, the sheet material comprising:

first and second faces;

a plurality of grooves formed in at least one of the first and second faces of the sheet material, said grooves intersecting each other to define a network of grooves defining passageways along the width and length of the sheet material to provide an outlet for heat and moisture dissipation for said body part being supported; and a plurality of cuts extending through the entire depth of said sheet material and distributed across the sheet material, whereby the center layer retaining structural integrity to provide orthopedic compression to the body part.

18. The sheet material according to claim 17, wherein said plurality of cuts are positioned primarily in registry with the grooves formed in the sheet material.

* * * * *

UNITED STATES PATENT AND TRADEMARK OFFICE
CERTIFICATE OF CORRECTION

PATENT NO. : 6,508,776 B2
DATED : January 21, 2003
INVENTOR(S) : J. Chiang et al.

It is certified that error appears in the above-identified patent and that said Letters Patent is hereby corrected as shown below:

Column 6,
Line 57, "any one of number" should read -- any one of any number --

Column 7,
Line 24, "composite materials" should read -- composite material --

Signed and Sealed this

Third Day of June, 2003

JAMES E. ROGAN
*Director of the United States Patent and Trademark Office*